United States Patent [19]

Wrobel et al.

[11] Patent Number: 5,221,686
[45] Date of Patent: Jun. 22, 1993

[54] SPIRO[1,2-BENZISOTHIAZOLE-3(2H),5'-OXAZOLIDINE]-2',4'-DIONE 1,1-DIOXIDES AS ANTIHYPERGLYCEMIC AGENTS

[75] Inventors: Jay E. Wrobel, Lawrenceville; Arlene Dietrich, Delran, both of N.J.

[73] Assignee: American Home Products Corporation, New York, N.Y.

[21] Appl. No.: 925,366

[22] Filed: Aug. 4, 1992

[51] Int. Cl.⁵ ............... A61K 31/42; C07D 513/10
[52] U.S. Cl. ............................. 514/373; 548/207
[58] Field of Search .................. 548/207; 514/373

[56] References Cited

U.S. PATENT DOCUMENTS

| | | | |
|---|---|---|---|
| 4,226,875 | 10/1980 | Schnur | 548/216 X |
| 4,864,028 | 9/1989 | York | 546/15 |
| 4,900,739 | 2/1990 | Wrobel | 514/373 |
| 4,927,831 | 5/1990 | Malamas | 514/278 |
| 4,980,357 | 12/1990 | Goldstein et al. | 514/278 |

FOREIGN PATENT DOCUMENTS

| | | |
|---|---|---|
| 0079675 | 5/1983 | European Pat. Off. . |
| 0097453 | 1/1984 | European Pat. Off. . |
| 0137333 | 4/1985 | European Pat. Off. . |

Primary Examiner—David B. Springer
Assistant Examiner—Fiona T. Powers
Attorney, Agent, or Firm—Walter Patton

[57] ABSTRACT

This invention relates to novel spiro[1,2-benzisothiazole-3(2H),5'-oxazolidine]-2',4'-dione 1,1-dioxides characterized by the general formula (I),

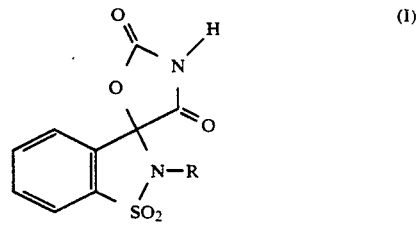

wherein R is lower alkyl containing 1 to 6 carbon atoms, cycloalkyl containing 5 to 6 carbon atoms, allyl, benzyl, halogen substituted benzyl, aralkyl containing 7 to 10 carbon atoms, halogen substituted aralkyl containing 7 to 10 carbon atoms; 3-phenyl-2-propynyl and halogen substituted 3-phenyl-2-propynyl and the pharmaceutically acceptable salts thereof, to the processes for their preparation, to methods for using the compounds, and to pharmaceutical compositions thereof. The compounds have pharmaceutical properties which render them beneficial for the treatment of diabetes mellitus and associated diabetic complications.

5 Claims, No Drawings

SPIRO[1,2-BENZISOTHIAZOLE-3(2H),5'-OXAZOLIDINE]-2',4'-DIONE 1,1-DIOXIDES AS ANTIHYPERGLYCEMIC AGENTS

BACKGROUND OF THE INVENTION

This invention relates to novel spiro[1,2-benzisothiazole-3(2H),5'-oxazolidine]-2',4'-dione 1,1-dioxides, to the processes for their preparation, to methods for using the compounds, and to pharmaceutical formulations thereof. The compounds have pharmaceutical properties which render them beneficial for the treatment of diabetes mellitus and associated diabetic complications.

Non-insulin dependent diabetes mellitus (Type II diabetes) is usually treated by a regiment including diet, exercise, oral agents such as sulfonylureas and, in more severe cases, insulin. Many of these hypoglycemic agents exhibit severe side effects. This, along with their generally limited efficacy, has created a need for new, novel and more potent antidiabetic agents which do not possess these drawbacks.

Ciglitazone [(+)-5-[4-[(1-methylcyclohexyl)methoxy]benzyl]thiazolidine-2,4-dione] is currently considered one of the most unique and promising drugs for treatment of hyperglycemia and hyperinsulinemia [Fujita et al, Diabetes, 32, 804 (1983)] because it only normalizes these parameters. The compounds of the present invention also possess antihyperglycemic activity and are of novel structure. Accordingly, the present compounds represent an important new approach for the treatment of diabetes mellitus.

Prior Art

Spiro[1,2-benzisothiazole-3(2H),3'-pyrroline]-2',5'-dione 1,1-dioxides, such as the compound of formula A

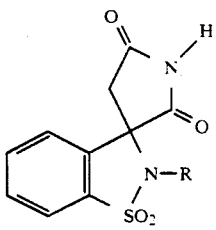

were claimed as aldose reductase inhibitors and antihyperglycemic agents [J. Wrobel U.S. Pat. No. 4,900,739 (1990)]. The compounds of the present invention differ from these in that the succinimide ring of A is replaced by an oxazolidine-2,4-dione ring.

Other disclosures claim compounds which contain an oxazolidine-2,4-dione ring and also show aldose reductase and/or antidiabetic activity. These include R. C. Schnur U.S. Pat. No. 4,226,875 (1980); A. J. Hutchinson European Patent Application 79,675 (1982); G. F. Holland European Patent Application 97,453 (1984); B. M. York, Jr. European Patent Application 137,333 (1985); B. M. York, Jr. U.S. Pat. No. 4,864,028 (1989); M. Malamas U.S. Pat. No. 4,927,831 (1990); and S. W. Goldstein, R. Sarges U.S. Pat. No. 4,980,357 (1991). None of the compounds from the above disclosures contain the 1,2-benzisothiazole-3-(2H), 1,1dioxide ring system possessed by the compounds of the present invention. In fact, the compounds of the present invention differ in that they are members of a novel ring system. Accordingly, the present compounds represent an important new approach for treatment of diabetes mellitus and associated diabetic complications.

SUMMARY OF THE INVENTION

This invention relates to novel spiro[1,2-benzisothiazole-3(2H),5'-oxazolidine]-2',4'-dione 1,1-dioxides of formula (I). These compounds possess antihyperglycemic activity in that they lower plasma glucose levels in the db/db (C57BL/KsJ) mouse, a model of human non-insulin dependent (Type II) diabetes mellitus. These compounds also possess aldose reductase inhibitor properties and therefore may be useful in the alleviation of diabetic complications.

The compounds of this invention are characterized by the general formula (I),

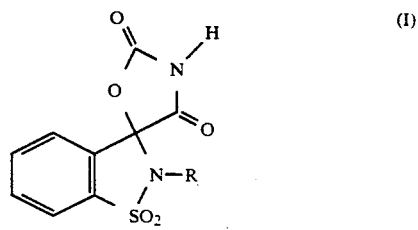

wherein R is lower alkyl containing 1 to 6 carbon atoms, cycloalkyl containing 5 to 6 carbon atoms, allyl, benzyl, halogen substituted benzyl, aralkyl containing 7 to 10 carbon atoms, halogen substituted aralkyl containing 7 to 10 carbon atoms; 3-phenyl-2-propynyl and halogen substituted 3-phenyl-2-propynyl and the pharmaceutically acceptable salts thereof.

Preferred compounds of this invention include compounds of formula (I) wherein R is halogen substituted benzyl.

The most preferred compounds of the present invention are designated:
2-[(4-bromo-2-fluorophenyl)methyl]spiro[1,2-benzisothiazole-3(2H),5'-oxazolidine]-2',4'-dione 1,1-dioxide:
2-[(4-bromophenyl)methyl]spiro[1,2-benzisothiazole-3(2H),5'-oxazolidine]-2',4'-dione 1,1-dioxide and the pharmaceutically acceptable salts thereof.

The compounds of formula (I) all possess at least one asymmetric carbon atom, namely the spiro carbon atom at position 5' of the oxazolidine ring. The compounds of formula (I) therefore exist, and may be isolated, in one or more racemic and optically active forms. This invention encompasses the compounds of formula (I) in racemic form or in any optically-active form.

Also included in the present invention are the chemical intermediate compounds of formula (Va), (VI) and (IX) described hereinafter.

The novel spiro[1,2-benzisothiazole-3(2H),5'-oxazolidine]-2',4'-dione 1,1-dioxides of this invention can be prepared by the processes described hereinafter.

A method is provided for preventing or relieving diabetes mellitus associated hyperglycemia in a diabetic mammal by administering to said mammal a prophylatic or alleviating amount of a compound of formula (I).

The compounds of the present invention may also be used as antihyperlipidemic or antihyperinsulinemic agents.

The compounds of formula (I), when admixed with a pharmaceutically acceptable carrier, form a pharmaceutical composition which can be used according to the preceding methods.

Detailed Description of the Invention

The compounds of formula (I) form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyl-triethanol and trimethyl-monoethanol) and cyclic ammonium salts, for example the N-methylpyridinium, N-methyl-N-(2-hydroxyethyl)morpholinium, N,N-dimethylmorpholinium, N-methyl-N-(2-hydroxyethyl)morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula (I) is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

The novel spiro[1,2-benzisothiazole-3(2H),5'-oxazolidine]-2',4'-dione 1,1-dioxides of this invention may be administered to mammals, for example, man, monkeys or dogs, either alone or in dosage forms, i.e., capsules or tablets, combined with pharmacologically acceptable excipients.

Advantageously, the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the spiro[1,2-benzisothiazole-3(2H),5'-oxazolidine]-2',4'-dione 1,1-dioxides will vary with the form of administration. Furthermore, it will vary with the particular host under treatment. Generally, treatment is initiated with small dosages substantially less than the optimal dose of the compound. In general, the compounds of this invention are most desirably administered at a concentration level that will generally afford effective results without causing any harmful or deleterious side effects. For topical administration, a 0.05–1.8% solution may be administered dropwise in the eye. The frequency of installation varies with the subject under treatment from a drop every two or three days to once daily. For oral or parenteral administration a preferred level of dosage ranges from about 0.5 mg to about 1000 mg per kilo of body weight per day, although aforementioned variations will occur. However, a dosage level that is in the range of from about 5.0 mg to about 60 mg per kilo of body weight per day is most satisfactory.

Unit dosage forms such as capsules, tablets, pills and the like may contain from about 25 mg to about 1250 mg of the active ingredients of this invention with a pharmaceutical carrier. Thus, for oral administration, capsules can contain from between about 25 mg to about 1250 mg of the active ingredients of this invention with or without a pharmaceutical diluent. Tablets, either effervescent or noneffervescent, can contain between about 25 to 1250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents for example, magnesium stearate.

Pharmacology

The blood glucose lowering activity of the compounds of this invention were demonstrable in experiments using diabetic (db/db) mice.

The db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia. Furthermore, the db/db mouse will eventually develop some of the long-term complications that have been associated with diabetes mellitus. [See Coleman Diabetes, 31(Suppl. 1), 1 (1982)]. In spite of these commonalities, the acute administration of sulfonylureas (even at extremely high dosages) will not reduce the hyperglycemia of the db/db mouse. [See Tutwiler et al, Diabetes 27, 856 (1978)]. The ability of a few other hypoglycemic agents to be effective in this species suggest that the other agents have mechanisms of action which are different from that of the sulfonylureas [ibid; Lee et al, Diabetes 31:12 (1982); Chang et al, Diabetes 32, 830 (1983); Hosokawa et al, Diabetes 34, 267 (1985)]. Such compounds, therefore, are more likely to be efficacious in the population of Type II diabetic patients that do not respond to sulfonylurea therapy. The experiments are exemplified hereinbelow after the listing of the following general procedure pertaining to these experiments.

On the morning of Day 1, 35 mice [male db/db (C57BL/KsJ), Jackson Laboratories, 2 to 7 months of age and body weight 35 to 60 g] were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels:

| Group A: | Vehicle control | N = 6 |
|---|---|---|
| Group B: | Positive control (ciglitazone) | N = 4 |
| Group C: | 1st Test drug | N = 4 |
| Group D: | 2nd Test drug | N = 4 |
| Group E: | 3rd Test drug | N = 4 |
| Group F: | 4th Test drug | N = 4 |
| Group H: | 5th Test drug | N = 4 |

On the afternoon of Days 1, 2 and 3 the vehicle, control or test drugs were administered (p.o.) to the ad libitum fed mice. The positive control, ciglitazone [($\pm$)-5-[4-[(1-methylcyclohexy]methoxy]benzyl]thiazolidine-2,4-dione] see Fujita et al, Diabetes, 32, 804 (1983), was given by gavage at a dose of 100 mg/kg/day. The test compounds were given by gavage at a dose of 100 mg/kg/day unless otherwise noted in the Table.

On the morning of Day 4, the mice were weighed and fasted, but water was available ad libitum. Three hours later, a blood sample was collected and then the mice were given the fourth administration of drug or vehicle. Blood samples were collected again from the unanesthetized mice at 2 and 4 hours after drug administration. The plasma was separated and levels of glucose in plasma determined by the Abbott VP Analyzer.

For each mouse, the percent change of it's plasma glucose level on Day 4 (mean of the 2 and 4 hour samples) from it's respective level before drug administration (Day 1 baseline sample) was determined as follows:

$$\frac{\text{Mean of 2 and 4 hour Samples(Day 4)}}{\text{Baseline Sample(Day 1)}} \times 100$$

Analysis of variance followed by Dunnett's multiple comparison (one-sided) was used to estimate the degree of statistical significance of the difference between the vehicle control group and the individual drug-treated groups. A drug was considered active, at the specific dosage administered, if the difference of the plasma glucose level has a $p<0.05$.

The tabulated results in the Table show that the spiro[1,2-benzisothiazole-3(2H),5'-oxazolidine]-2',4'-dione 1,1-dioxides of this invention show the property that they lower blood glucose levels in the postprandial diabetic (db/db) mice. The actual difference between the mean percent change of the vehicle and the drug-treated group is reported in the Table.

Examination of the results tabulated in the Table below shows that the spiro[1,2-benzisothiazole-3(2H),5'-oxazolidine]-2',4'-dione 1,1-dioxides of this invention are well suited as antihyperglycemic agents for they lower blood glucose levels in diabetic mice. For example, 2-[(4-bromo-2-fluorophenyl)methyl]-2,3-dihydrospiro[1,2-benzisothiazole-3,3'-pyrrolidine]-2',5'-dione 1,1-dioxide, the compound of Example 2, at a dose of 100 mg/kg gives comparable results to ciglitazone at 100 mg/kg.

TABLE
Chemical and Biological Data

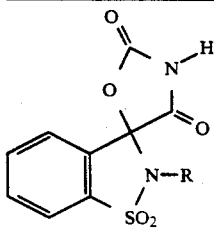

(I)

| Example | R— | Prepared According to Scheme | Analysis Calc C, H, N Found C, H, N | mp °C. | % Glucose Decrease at 100 mg/kg Dose |
|---|---|---|---|---|---|
| 1 | t-butyl | I | $C_{13}H_{14}N_2O_5S$ | 135–136 | * |

TABLE-continued

Chemical and Biological Data (I)

| Example | R— | Prepared According to Scheme | Analysis Calc C, H, N Found C, H, N | mp °C. | % Glucose Decrease at 100 mg/kg Dose |
|---|---|---|---|---|---|
| | | | 50.32, 4.55, 9.03 50.34, 4.53, 8.88 | | |
| 2 | (4-bromo-2-fluoro-phenyl)methyl | II | $C_{19}H_{10}BrFN_2O_5S$ 43.55, 2.29, 6.35 43.42, 2.43, 6.15 | 269–270 (dec) | 44 |
| 3 | (4-bromophenyl)-methyl | III | $C_{16}H_{11}BrN_2O_5S$ 45.40, 2.62, 6.62 45.65, 2.64, 6.88 | 220–260 (dec) | 16 |
| 4 | methyl | I | $C_{10}H_8N_2O_5S$ 44.78, 3.01, 10.44 44.70, 2.92, 10.61 | 290–300 (dec.) | * |
| 5 | 2-propyl | I | $C_{12}H_{12}N_2O_5S$ 48.64, 4.08, 9.45 48.78, 4.17, 9.30 | 264–266 (dec) | * |
| 6 | phenylmethyl | I | $C_{16}H_{12}N_2O_5S$ 55.81, 3.51, 8.13 55.67, 3.55, 7.95 | 266–269 (dec) | * |
| 7 | 3-(4-chloro)phenyl-2-propynyl | II | $C_{18}H_{11}ClN_2O_5S \cdot 0.5H_2O$ 52.48, 2.94, 6.80 52.43, 3.06, 6.78 | 273–276 (dec) | * |
| 8 | 3-pentyl | I | $C_{14}H_{16}N_2O_5S$ 51.84, 4.97, 8.64 51.71, 4.93, 8.46 | 238–240 (dec) | * |
| 9 | cyclopentyl | I | $C_{14}H_{14}N_2O_5S$ 52.17, 4.38, 8.69 52.04, 4.31, 8.45 | 255–290 (dec) | * |
| 10 | 2-propenyl | I | $C_{12}H_{10}N_2O_5S$ 48.98, 3.42, 9.52 48.86, 3.48, 9.29 | 290–293 (dec) | * |
| 11 | cyclohexyl | I | $C_{15}H_{16}N_2O_5S$ 55.56, 4.79, 8.33 55.46, 4.78, 8.73 | 260–265 (dec) | * |
| 12 | 4-(4-chloro)phenyl-butyl | I | $C_{19}H_{17}ClN_2O_5S$ 54.22, 4.07, 6.66 54.16, 4.17, 6.50 | 70–71 | * |

*<15% decrease at 100 mg/kg Ciglitazone (reference standard) 100 mg/kg 33

The Process

The 2-benzisothiazole-3(2H),5'-oxazolidine]-2',4'-dione 1,1-dioxides of this invention can be prepared by the following reaction schemes:

Scheme I

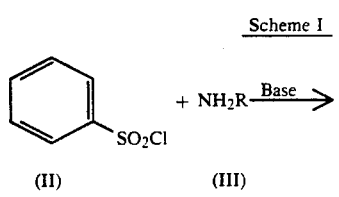

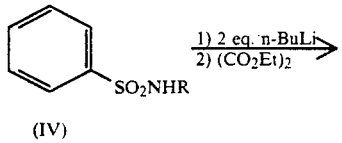

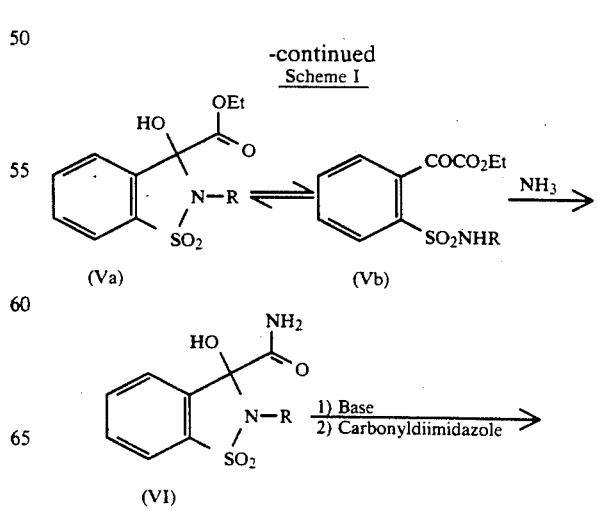

-continued
Scheme I

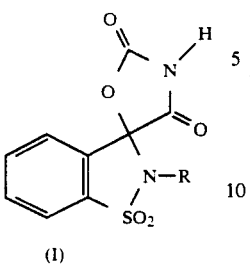

(I)

Scheme II

[(V), R = tBu] —HCO₂H→

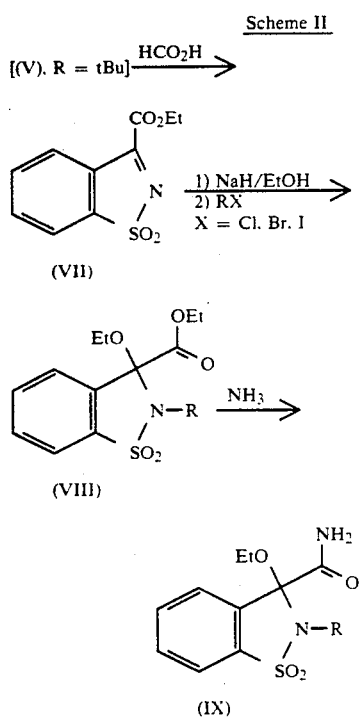

Wherein R is as defined above.

Scheme III

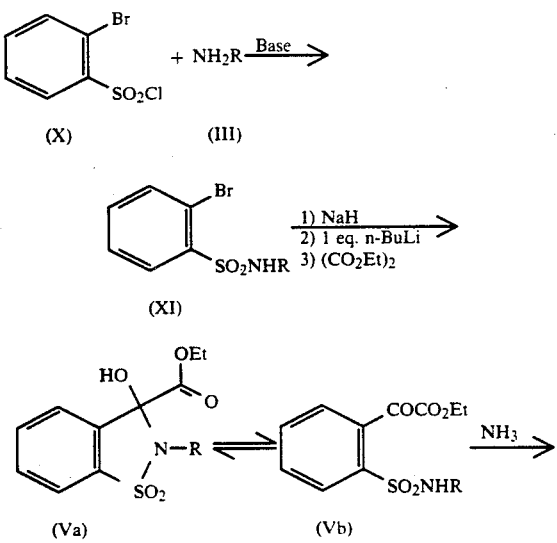

-continued
Scheme III

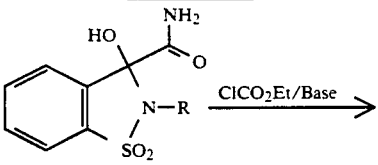

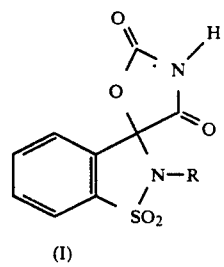

(I)

Wherein R is as defined above.

The compounds of this invention can be prepared according to the methods outlined in Schemes I, II and III. Referring to Scheme I, commercially available benzenesulfonyl chloride (II) can be reacted with the appropriate commercially available amine of formula (III), wherein R is as defined above. The reaction is performed in the presence of an amine base such as triethylamine, pyridine or 4-dimethylaminopyridine to produce the benzenesulfonamide of formula (IV). The reaction is most conveniently performed in an organic solvent such as dichloromethane, chloroform or tetrahydrofuran at 0° C. to room temperature.

The compound of formula (IV) is then treated with at least two molar equivalents of n-butyllithium in tetrahydrofuran solvent at 0° C. to room temperature and the resultant dilithio species is reacted with diethyloxalate at −78° C. to room temperature to produce the compound of formula (V). The compounds of formula (V) can exist in opened [structure (Va)] or closed [structure (Vb)] ring forms or an equilibrium mixture of both (Va) and (Vb). The steric bulk of the nitrogen R-group determines the relative percentage of (Va) or (Vb). Thus compounds with small R-groups, such as $CH_3$, exist primarily as (Va) and compounds with sterically demanding R-groups, such as t-butyl exist primarily in the open form (Vb).

The compound of formula (V) is then treated with ammonia to produce the primary amide of formula (VI). This reaction is most conveniently performed in alcoholic solvent such as ethanol or methanol, generally at ambient temperatures. Unlike the esters of formula (V), amides of formula (VI) generally appear to exist primarily in the closed form.

The amide of formula (VI) is then treated with at least two molar equivalents of a base such as sodium hydride, n-butyllithium, lithium diisopropyl amine or lithium, sodium or potassium bis(trimethylsilyl)amide at 0° C. in tetrahydrofuran solvent or a mixture of tetrahydrofuran and hexane. The resultant dimetallated species is then reacted with carbonyldiimidazole ultimately to produce the compound of formula (I) after an aqueous acid workup procedure.

Alternatively, the compounds of formula (I) can be prepared by the methods outlined in Scheme II. The compound of formula (V) in which R is t-butyl, prepared according to Scheme I, is treated with formic acid. The formic acid removes the t-buyl moiety and the resultant species undergoes a cyclization with loss of water to afford the ethyl ester of formula (VII).

The compound of formula (VII) is then treated with one molar equivalent of a metal ethoxide, such as sodium ethoxide or potassium ethoxide. This is most conveniently generated by treating one molar equivalent of ethanol with one molar equivalent of sodium hydride in dimethylformamide or dimethylsulfoxide solvent at 0° C. to room temperature for a period of 10 minutes to one hour in the presence of the compound of formula (VII). The metal ethoxide adds to the carbon-nitrogen double bond of (VII) to generate an intermediate metallated sulfonamide. An alkylating agent RX is then introduced into the reaction media, wherein R is as defined above and X is halogen (chlorine, bromine or iodine). Alkylation occurs on the sulfonamide nitrogen to afford the α-ethoxyester of formula (VIII).

The α-ethoxyester of formula (VIII) is then treated with ammonia to produce the primary amide of formula (IX). This reaction is most conveniently performed in alcoholic solvent such as ethanol or methanol, generally at ambient temperatures.

The α-ethoxyamide of formula (IX) is hydrolyzed to the corresponding α-hydroxyamide of formula (VI) employing aqueous mineral acids, such as aqueous hydrochloric acid or sulfuric acid with a water miscible organic solvent, such as terahydrofuran or 1,4-dioxane. The reaction is most conveniently done at temperatures between 50° C. and 100° C. for two to eight hours. The compounds of formula (VI) are then used to prepare the compounds of formula (I) by the process outlined in Scheme I.

Still alternatively, the compounds of formula (I) can be prepared according to the methods outlined in Scheme III. Commercially available 2-bromobenzenesulfonyl chloride (X) can be reacted with the appropriate commercially available amine of formula (III), wherein R is as defined above. The reaction is performed in the presence of an amine base such as triethylamine, pyridine or 4-dimethylaminopyridine to produce the benzenesulfonamide of formula (XI). The reaction is most conveniently performed in an organic solvent such as dichloromethane, chloroform or tetrahydrofuran at 0° C. to room temperature.

The sulfonamide of formula (XI) is then reacted with a alkali-metal hydride, such as sodium hydride in a solvent such as tetrahydrofuran at room temperature to 80° C. in order to cause deprotonation of the sulfonamide NH of (XI). The resultant compound is then treated with one molar equivalent of n-butyllithium at lower temperatures (−78° to 0° C.) in order to effect lithium-bromine exchange and the resultant dimetallated sulfonamide is reacted with diethyloxalate at −78° C. to room temperature to produce the compound of formula (V). As is Scheme I, the ester of formula (V) is treated with ammonia to produce the primary amide of formula (VI).

The α-hydroxyamide of formula (V) is reacted with ethyl chloroformate in the presence of an amine base such as triethylamine and/or N,N-dimethylaminopyridine to afford the compound of formula (I). The reaction is most conveniently performed in an organic solvent such as dichloromethane or tetrahydrofuran, starting at low temperatures, then gradually heating to 50° to 80° C.

Further, when an optically-active form of a compound of formula (I) is required, a racemic form of said compound may be reacted with an optically active form of a suitable organic base, for example, brucine, coniine, 2-pipecoline or N,N,N-trimethyl-(1-phenylethyl)ammonium hydroxide followed by conventional separation of the diasteriomeric mixture of salts or complexes thus obtained, for example, by fractional crystallization from a suitable solvent, for example, a lower alkanol, whereafter the optically active form of said compound may be liberated by treatment with acid using a conventional procedure, for example, using an aqueous mineral acid such as dilute hydrochloric acid.

The following Examples further illustrate this invention.

EXAMPLE 1

Step 1: N-1,1-Dimethylethylbenzenesulfonamide [(IV), R=tBu]

Benzenesulfonyl chloride [(II), 3.0 mL, 23.51 mmol] was added to a cold (0° to 5° C.) solution of tert-butylamine [(III), 3.7 mL, 35.26 mmol], triethylamine (6.6 mL, 47.02 mmol), 4-dimethylaminopyridine (0.570 g, 4.70 mmol) and methylene chloride (22 mL) under a dry nitrogen atmosphere. After stirring for 2 hours the methylene chloride was removed and the reaction mixture was partitioned between 2N HCl (120 mL) and ether (250 mL). The ether phase was washed with brine, dried over $MgSO_4$, concentrated, and dried in vacuo to give the title compound as a white solid, (4.61 g, 92%): NMR ($CDCl_3$, 300 MHz): d 1.23 (s, 9H, C(C$\underline{H}_3)_3$), 7.51 (m, 3H, Ar$\underline{H}$), 7.90 (m, 2H, Ar$\underline{H}$).

Step 2: 2-[1,1-Dimethylethyl]-2,3-dihydro-3-hydroxy-1,2-benzisothiazole-3-carboxylic Acid Ethyl Ester 1,1-Dioxide [(V), R=tBu]

n-Butyllithium (16.14 mL, 40.36 mmol, 2.5N in hexane) was added dropwise over a 20 minute period to a cold (0° to 5° C.), mechanically stirred solution of [(IV), R=tBu] (4.2 g, 19.69 mmol) in anhydrous tetrahydrofuran (118 mL) under a dry nitrogen atmosphere. After stirring an additional 25 minutes at 0° to 5° C. a precipitate formed. The suspension was cooled further to −78° C. and diethyloxylate was added. The cooling bath was removed and the suspension was stirred at ambient temperature for 17 minutes and dissolution occurred. The reaction was quenched with 5% HCl (40 mL) and added to water (200 mL). The organics were extracted with ether (200 mL). The ether phase was washed with brine (200 mL) and silica gel (50 mL) was added. The solvent was removed and the adsorbate was flash chromatographed (7:3 petroleum ether: ethyl acetate) to give the title compound as an off white solid, (5.51 g, 89%): m.p. 93°–95° C.; NMR ($CDCl_3$, 300 MHz): d 1.27 (s, 9H, C(C$\underline{H}_3)_3$), 1.41 (t, 3H, $CH_2C\underline{H}_3$ J=7 Hz), 4.41 (dd, 2H, C$\underline{H}_2$CH$_3$, J=7 Hz), 5.01 (s, 1H, SO$_2$N$\underline{H}$), 7.64 (m, 3H, Ar$\underline{H}$), 8.03 (m, 1H, Ar$\underline{H}$); IR (KBr, cm$^{-1}$): 3400, 3285, 1735, 1705; MS (CI, m/z): 314 (18%), 258 (65%), 240 (100%), 241 (18%); Anal. ($C_{14}H_{19}NO_5S$): C, H, N.

Step 3:
2-[1,1-Dimethylethyl]-2,3-dihydro-3-hydroxy-1,2-benzisothiazole-3-carboxamide Acid Ethyl Ester 1,1-Dioxide [(VI), R=tBu]

The compound of formula [(V), R=tBu] (2.5 g, 7.98 mmol) was added to a saturated solution of ammonia in methanol. The flask was sealed and stirred at 0° C. for 25 minutes before warming to room temperature. After stirring one hour the solvent was removed and the resulting solid was triturated with ether and filtered to give the title compound as an off white solid, (2.15 g, 95%): mp 139.5°–140.5° C.; NMR (DMSO d6, 300 MHz): d 1.51 (s, 9H, (CH$_3$)$_3$), 7.68 (m, 6H, ArH and NH$_2$), 7.90 (s, 1H, OH); IR (KBr, cm$^{-1}$): 3420, 3310, 1685, 1595; MS (+FAB, m/z): 307 (70%, MNa+), 285 (20%, MH+), 229 (40%), 212 (100%); Anal. (C$_{12}$H$_{16}$N$_2$O$_4$S): C, H, N.

Step 4:
2-(1,1-Dimethylethyl)spiro[1,2-benzisothiazole-3(2H),5'-oxazolidine]-2',4'-dione 1,1-Dioxide [(I), R=tBu]

Lithium bis(trimethylsilyl)amide (14.76 mL, 14.76 mmol, 1.0N in hexanes) was added dropwise to a 0° to 5° C., mechanically stirred suspension of [(VI), R=tBu] (2.0 g, 7.03 mmol) in tetrahydrofuran (18 mL) over a 10 minute period under a dry nitrogen atmosphere. Dissolution occurred. After stirring an additional 30 minutes at 0° to 5° C., a solution of carbonyldiimidazole (2.85 g, 17.58 mmol) in tetrahydrofuran (55 mL) was added dropwise over a 6 minute period. A suspension immediately resulted. The suspension was stirred at room temperature for 17.5 hours. The reaction mixture was cooled to 0° to 5° C. and 10% HCl (45 mL) was added. The reaction mixture was added to water (120 mL) and more 10% HCl (20 mL) was added. The organics were extracted with ethyl acetate (200 mL) and the solvent was removed. A solution of saturated aqueous NaHCO$_3$ (85 mL) and water (60 mL) was added to the concentrate which was then partitioned with ether (200 mL). The layers were separated and the aqueous phase was washed with ether (2×100 mL). The aqueous phase was cooled in an ice bath and carefully acidified with concentrated HCl. The semisolid which precipitated was extracted with ethyl acetate (200 mL). The ethyl acetate phase was washed with brine, dried over MgSO$_4$ and concentrated to give a foamy solid (1.31 g, 60%). This solid was stirred as a suspension in petroleum ether (300 ml) for 45 hours then filtered and dried in vacuo to give the title compound as a white solid (1.19 g, 55%): mp 135°–136° C.; NMR (DMSO d6, 400 MHz): d 1.55 (s, 9H, (CH$_3$)$_3$), 7.86 (m, 3H, ArH), 8.05 (m, 1H, ArH), 13.25 (broad s, 1H, NH); IR (KBr, cm$^{-1}$): 3250, 1835, 1775; MS (+FAB, m/z): 311 (5%, MH+), 255 (50%), 211 (27%), 157 (15%), 57 (90%); Anal. (C$_{13}$H$_{14}$N$_2$O$_5$S): C, H, N.

EXAMPLE 2

Step 1: 1,2-Benzoisothiazole-3-carboxylic Acid Ethyl Ester 1,1-Dioxide (VII)

Formic acid (25 mL) was added to [(V), R=tBu] (2.45 g, 7.82 mmol) and the suspension was stirred at room temperature under a dry nitrogen atmosphere. After 5 minutes dissolution occurred. After 20 hours the solution was concentrated and the resultant solid was dissolved in CH$_2$Cl$_2$ and concentrated (three times) to remove traces of formic acid. This afforded the title compound as a white solid (1.85 g, 98%). A small portion of this material was further purified by flash chromatography (7:3 petroleum ether: ethyl acetate): mp 114°–115° C.; NMR (CDCl$_3$, 300 MHz): d 8.32 (dd, 1H, J=1.1, 3.1 Hz, ArH), 7.96 (dd, 1H, J=1.1, 3.1 Hz, ArH), 7.79 (m, 2H, ArH), 4.55 (q, 2H, J=7.2 Hz, CH$_2$), 1.49 (t, 3H, J=7.2 Hz, CH$_3$); IR (KBr, cm$^{-1}$): 1735, 1555; MS (EI, m/z): 239 (M, 3%), 195 (20%), 102 (100%); Anal. (C$_{10}$H$_9$NO$_4$S): C, H, N.

Step 2:
2-[(4-Bromo-2-fluorophenyl)methyl]-2,3-dihydro-3-ethoxy-1,2-benzisothiazole-3-carboxylic Acid Ethyl ester 1,1-Dioxide [(VIII), R=(4-Bromo-2-fluorophenyl)methyl]

Sodium hydride (0.21 g, 7.02 mmol, 80% dispersion in mineral oil) was added to a stirred, room temperature solution of (VII) (1.40 g, 5.85 mmol) and dry ethanol (0.38 mL), 6.44 mmol) in DMF (8 mL). An exotherm resulted and after 10 min, 4-bromo-2-fluorobenzyl bromide (1.72 g, 6.44 mmol) was added. After 2 h, the reaction mixture was added to an aqueous solution consisting of 10% aq. HCl (25 mL) and water (125 mL). This was extracted with ether (150 mL) and the ether extract was washed with brine (150 mL) and silica gel (25 mL) was added to it. The ether was removed and the silica adsorbate was flash chromatographed (7:3 petroleum ether: ethyl acetate) to provide the title compound as an oil (1.89 g, 68%): NMR (CDCl$_3$, 300 MHz): d 7.89 (m, 1H, ArH), 7.70 (m, 2H, ArH), 7.55 (m, 2H, ArH), 7.26 (m, 2H, ArH), 4.60 (d, 1H, J=16.7 Hz, NCH$_2$), 4.50 (d, 1H, J=16.7 Hz, NCH$_2$), 4.05 (m, 2H, CO$_2$CH$_2$), 3.22 (m, 1H, OCH$_2$), 2.94 (m, 1H, OCH$_2$), 1.11 (t, 3H, CH$_3$), 1.05 (t, 3H, CH$_3$); IR (neat, cm$^{-1}$): 1750: MS (+FAB): 472, 474 (MH+, 5%), 426, 428 (35%), 398, 400 (20%), 187, 189 (100%).

Step 3:
2-[(4-Bromo-2-fluorophenyl)methyl]-2,3-dihydro-3-ethoxy-1,2-benzisothiazole-3-carboxamide 1,1-Dioxide [(IX), R=(4-Bromo-2-fluorophenyl)methyl]

The compound of formula [(VIII), R=(4-bromo-2-fluorophenyl)methyl] (1.89 g, 4.00 mmol) was added to a saturated solution of ammonia in methanol at 0° C. This solution was stirred at room temperature for 4 hours then the solvent was removed and the resulting solid was dissolved in CH$_2$Cl$_2$ and concentrated (three times) to remove traces of methanol to give the title compound as a white solid, (1.77 g, 100%): mp 175°–177° C.; NMR (DMSO d6, 300 MHz): d 8.00–7.40 (m, 9H, ArH, NH$_2$), 4.51 (d, 1H, J=16.1 Hz, NCH$_2$), 4.23 (d, 1H, J=16.1 Hz, NCH$_2$), 3.01 (m, 1H, OCH$_2$), 2.82 (m, 1H, OCH$_2$), 0.84 (t, 3H, CH$_3$); IR (KBr, cm$^{-1}$): 1710; MS (+FAB): 465, 466 (MNa+, 25%), 399, 401 (15%), 187, 189 (100%).

Step 4:
2-[(4-Bromo-2-fluorophenyl)methyl]-2,3-dihydro-3-hydroxy-1,2-benzisothiazole-3-carboxamide 1,1-Dioxide [(VI), R=(4-Bromo-2-fluorophenyl)methyl]

A mixture of [(IX), R=(4-bromo-2-fluorophenyl)methyl] (1.73 g, 3.90 mmol), 1,4-dioxane (15 mL), 10% aq. HCl (5 mL) and conc. H$_2$SO$_4$ (1 mL) were heated with stirring in a 60° C. oil bath for 5 hours. The mixture was cooled to room temperature and added to water (200 mL). The water phase was extracted with ethyl acetate (200 mL) and the ethyl acetate extracts were washed with saturated aq. NaHCO$_3$ (4×100 mL), dried (brine, then MgSO$_4$) and concentrated to provide the title compound as a white solid (1.16 g, 72%): mp 182°-184° C.; NMR (DMSO d6, 300 MHz): d 8.0-7.3 (m, 10H, ArH, OH, NH$_2$), 4.54 (d, 1H, J=16.7 Hz, NCH$_2$), 4.24 (d, 1H, J=16.7 Hz, NCH$_2$); IR (KBr, cm$^{-1}$): 3450, 3340, 1695; MS (+FAB): 437, 439 (MNa+, 10%), 415, 417 (MH+, 5%), 399, 401 (10%); Anal. (C$_{15}$H$_{12}$BrFN$_2$O$_4$S): C, H, N.

Step 5:
2-[(4-Bromo-2-fluorophenyl)methyl]spiro[1,2-benzisothiazole-3(2H),5'-oxazolidine]-2',4'-dione 1,1-Dioxide [(I), R=(4-Bromo-2-fluorophenyl)methyl]

Lithium bis(trimethylsilyl)amide (5.0 mL, 5.0 mmol, 1.0N in hexanes) was added dropwise to a 0° to 5° C., mechanically stirred suspension of [(VI), R=(4-bromo-2-fluorophenyl)methyl] (0.98 g, 2.36 mmol) in tetrahydrofuran (8 mL) over a 10 minute period under a dry nitrogen atmosphere. Dissolution occurred. After stirring an additional 20 minutes at 0° to 5° C., a solution of carbonyldiimidazole (0.96 g, 5.90 mmol) in tetrahydrofuran (20 mL) was added dropwise over a 10 minute period. A suspension immediately resulted. The suspension was stirred at room temperature for 4 hours. The reaction mixture was cooled to 0° to 5° C. and 10% HCl (15 mL) was added. The reaction mixture was added to water (100 mL), extracted with ethyl acetate (120 mL) and the solvent was removed. A solution of saturated aqueous NaHCO$_3$ (40 mL) and water (30 mL) was added to the concentrate which was then partitioned with ether (100 mL). The layers were separated and the aqueous phase was washed with ether (2×100 mL). The aqueous phase was cooled in an ice bath and carefully acidified with concentrated HCl. The semisolid which precipitated was extracted with ethyl acetate (120 mL). The ethyl acetate phase was washed with brine, dried over MgSO$_4$, and concentrated to give the title compound as a white solid (0.73 g, 70%). This solid was stirred as a suspension in petroleum ether (350 mL) overnight, then filtered and dried in vacuo to remove traces of solvent from the title compound: mp 269°-270° C. (dec); NMR (DMSO d6, 400 MHz): d 13.05 (bs, 1H, NH), 8.19 (m, 1H, ArH), 7.96 (m, 1H, ArH), 7.91 (m, 2H, ArH), 7.57 (dd, 1H, J=1.8, 9.8 Hz, ArH), 7.45 (dd, 1H, J=1.8, 8.3 Hz, ArH), 7.38 (t, 1H, J=8.3 Hz, ArH), 4.58 (d, 1H, J=15.6 Hz, NCH$_2$), 4.53 (d, 1H, J=15.6 Hz, NCH$_2$); IR (KBr, cm−1): 3150-3600, 1830, 1765; MS (+FAB): 463, 465 (MNa+, 10%), 441, 443 (MH+, 10%); Anal. (C$_{16}$H$_{10}$BrFN$_2$O$_5$S) C, H, N.

EXAMPLE 3

Step 1:
N-[(4-Bromophenyl)methyl]-2-bromobenzenesulfonamide [(XI), R=(4-bromophenyl)methyl]

2-Bromobenzenesulfonyl chloride [(X), 5.9 g, 23.5 mmol] was added dropwise to a stirred 0° C. suspension of 2-bromobenzylamine hydrochloride [(II), R=(4-bromophenyl)methyl, 4.79 g, 19.6 mmol], pyridine (7.9 mL, 97.9 mmol) and 4-dimethylaminopyridine (0.23 g, 1.96 mmol) in dichloromethane (10 mL). The reaction mixture was then stirred at room temperature for 1 hour, then triethylamine (2.73 mL, 19.6 mmol) was then added at 0° C. After stirring overnight at room temperature, the reaction was diluted with dichloromethane (100 mL) then washed with water (50 mL), 0.5N HCl (2×50 mL), water (50 mL), saturated aq. NaHCO$_3$ (2×50 mL) and water (50 mL). The dichloromethane solution was dried (brine, MgSO$_4$) and silica gel (80 mL) was added. The solution was concentrated and the adsorbate was flash chromatographed (4:1 petroleum ether:ethyl acetate) to provide the title compound as a white solid (5.92 g, 75%): mp 108°-110° C.; NMR (CDCl$_3$, 300 MHz): d 8.08 (m, 1H, ArH), 7.70 (m, 1H, ArH), 7.55-7.30 (m, 4H, ArH), 7.08 (d, 2H, ArH), 5.42 (t, 1H, NH), 4.07 (d, 2H, CH$_2$); Anal. (C$_{13}$H$_{11}$Br$_2$NO$_2$S) C, H, N.

Step 2:
2-[(4-Bromophenyl)methyl]-2,3-dihydro-3-hydroxy-1,2-benzisothiazole-3-carboxylic Acid Ethyl Ester 1,1-Dioxide [(V), R=(4-bromophenyl)methyl]

Sodium hydride (0.44 g, 14.81 mmol) was added to a stirred, room temperature solution of [(XI), R=(4-bromophenyl)methyl] (5.0 g, 12.34 mmol) in tetrahydrofuran under a dry nitrogen atmosphere. After foaming subsided, the reaction mixture was heated in a 50° C. oil bath for 5 minutes, then cooled to −78° C. whereupon an additional amount of THF was added (45 mL). n-Butyllithium (5.0 mL, 12.34 mmol, 2.46M solution in hexane) was added over a 25 minute period. After an additional 20 minutes, diethyloxalate (8.4 mL, 61.8 mmol) was added and the cold bath was removed. The reaction mixture was allowed to warm over a 25 minute period, then quenched carefully with 5% HCl. The reaction mixture was then quickly added to water (400 mL) and extracted with ether (400 mL). The ether phase washed with brine (200 mL) and silica gel (30 mL) was added. The reaction mixture was concentrated and the adsorbate was flash chromatographed (gradient, 4:1 to 7:3 to 3:2 to 1:1 petroleum ether:ethyl acetate) to provide the title compound as a white solid (2.61 g, 50%): mp 152°-153° C.; NMR (CDCl$_3$, 400 MHz): d 7.90 (m, 1H, ArH), 7.68 (m, 2H, ArH), 7.46 (m, 2H, ArH), 7.36 (m, 3H, ArH), 4.90 (s, 1H, OH), 4.56 (d, 1H, J =16.0 Hz, NCH$_2$), 4.35 (d, 1H, J=16.0 Hz, NCH$_2$), 3.92 (dq, 1H, OCH$_2$), 3.70 (dq, 1H, OCH$_2$), 1.01 (t, 3H, OCH$_2$CH$_3$); IR (KBr, cm$^{-1}$): 3440, 1725; MS (EI): 379, 381 (M-EtOH, 2%), 352, 354 (8%), 315, 317 (11%), 169, 171 (100%); Anal. (C$_{17}$H$_{16}$BrNO$_5$S) C, H, N.

Step 3:
2-[(4-Bromophenyl)methyl]-2,3-dihydro-3-hydroxy-1,2-benzisothiazole-3-carboxamide 1,1-Dioxide [(VI), R=(4-bromophenyl)methyl]

The compound of formula [(V), R=(4-bromophenyl)methyl] (1.56 g, 3.66 mmol) was added to a saturated solution of ammonia in methanol at 0° C. This solution was stirred at room temperature for 3 hours then the solvent was removed and the resulting solid was dissolved in CH$_2$Cl$_2$ and concentrated (three times) to remove traces of methanol to give the title compound as a white solid, (1.41 g, 97%): mp 166°-168° C.; NMR (DMSO d6, 300 MHz): d 7.90-7.30 (m, 10H, ArH, NH$_2$, OH), 4.40 (d, 1H, J=16.1 Hz, NCH$_2$), 4.13 (d, 1H, J=16.1 Hz, NCH$_2$); IR (KBr, cm$^{-1}$): 3470, 3230, 1695; MS (+FAB): 421, 423 (MNa+, 10%), 397, 399 (MH+, 10%), 381, 383 (20%).

Step 4:

2-[(4-Bromophenyl)methyl]spiro[1,2-benzisothiazole-3(2H),5-oxazolidine]-2',4'-dione 1,1-Dioxide [(I), R=(4-bromophenyl)methyl]

Ethyl chloroformate (0.31 mL, 3.24 mmol) was added dropwise to a 0° C., stirred suspension of [(VI), R=(4-bromophenyl)methyl] (1.15 g, 2.90 mmol), triethylamine (0.49 mL, 3,48 mmol), dimethylaminopyridine (70 mg, 0.58 mmol) and tetrahydrofuran (7.5 mL). The resultant suspension was stirred at room temperature for 1.5 hours then heated in a 70° C. oil bath for 2.5 hours. The suspension was then cooled in an ice bath and acidified with 10% HCl. Water (50 mL) and ethyl acetate (50 mL) were added and the layers were shaken then separated. The ethyl acetate layer was concentrated then dilute aq.NaHCO$_3$ (70 mL) and ether (70 mL) were added. The layers were separated and the NaHCO$_3$ layer was extracted with more ether (40 mL). The NaHCO$_3$ layer was cooled in an ice bath and carefully acidified with concentrated HCl. The resultant solid was filtered, washed with water and dried in vacuo to provide the title compound as a white solid (0.37 g, 30%): mp 220°-260° C. (dec); NMR (DMSO d6, 400 MHz): d 13.10 (bs, 1H, N$\underline{H}$), 8.20 (m, 1H, Ar$\underline{H}$), 7.98 (m, 1H, Ar$\underline{H}$), 7.91 (m, 2H, Ar$\underline{H}$), 7.55 (m, 2H, Ar$\underline{H}$), 7.35 (m, 2H, Ar$\underline{H}$), 4.57 (d, 1H, J=16.2 Hz, NC$\underline{H}_2$), 4.52 (d, 1H, J=16.2 Hz, NC$\underline{H}_2$); IR (KBr, cm$-1$): 3000-3700, 1835, 1770; MS (+FAB): 423, 425 (MH+, 10%), 169, 171 (30%); Anal. (C$_{16}$H$_{11}$BrN$_2$O$_5$S) C, H, N.

We claim:

1. A compound of formula (I)

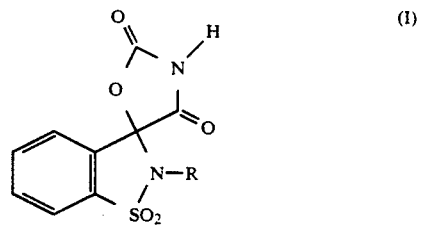

wherein R is halogen substituted benzyl or a pharmaceutically acceptable salt thereof.

2. The compound according to claim 1, designated 2-[(4-bromo-2-fluorophenyl)methyl]spiro[1,2-benzisothiazole-3(2H),5'-oxazolidine]-2',4'-dione 1,1-dioxide or a pharmaceutically acceptable salt thereof.

3. The compound according to claim 1, designated 2-[(4-bromophenyl)methyl]spiro[1,2-benzisothiazole-3(2H),5'-oxazolidine]-2',4'-dione 1,1-dioxide or a pharmaceutically acceptable salt thereof.

4. A pharmaceutical composition for relieving hyperglycemia in a diabetic mammal, which comprises an alleviating amount of a compound of claim 1 and a pharmaceutically acceptable carrier.

5. A method of relieving hyperglycemia in a diabetic mammal, which comprises administering to said mammal an alleviating amount of a compound of claim 1.

* * * * *